US011500359B1

(12) United States Patent
Fernando

(10) Patent No.: US 11,500,359 B1
(45) Date of Patent: *Nov. 15, 2022

(54) IMMUNITY TRACKING SYSTEM

(71) Applicant: Art Research and Technology, L.L.C., Phoenix, AZ (US)

(72) Inventor: Barry Fernando, Phoenix, AZ (US)

(73) Assignee: ART RESEARCH AND TECHNOLOGY, L.L.C., Phoenix, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/669,071

(22) Filed: Feb. 10, 2022

Related U.S. Application Data

(63) Continuation of application No. 17/329,771, filed on May 25, 2021, now Pat. No. 11,281,194.

(51) Int. Cl.
| | |
|---|---|
| *G05B 19/00* | (2006.01) |
| *G05B 19/418* | (2006.01) |
| *G16H 10/40* | (2018.01) |
| *G16H 10/60* | (2018.01) |

(52) U.S. Cl.
CPC ....... *G05B 19/41865* (2013.01); *G16H 10/40* (2018.01); *G16H 10/60* (2018.01)

(58) Field of Classification Search
CPC ............. G05B 19/41865; G16H 10/40; G16H 10/60
See application file for complete search history.

(56) References Cited

U.S. PATENT DOCUMENTS

| | | | |
|---|---|---|---|
| 10,895,580 B2 * | 1/2021 | Maetzler | G01N 35/00871 |
| 2006/0045806 A1 * | 3/2006 | Winther | G01N 1/312 422/68.1 |
| 2018/0340949 A1 * | 11/2018 | Maetzler | G01N 35/00732 |

OTHER PUBLICATIONS

USPTO, Restriction/Election Requirement dated Aug. 11, 2021 in U.S. Appl. No. 17/329,771.
USPTO, Non-Final Office Action dated Oct. 18, 2021 in U.S. Appl. No. 17/329,771.
USPTO, Notice of Allowance dated Feb. 10, 2022 in U.S. Appl. No. 17/329,771.

* cited by examiner

*Primary Examiner* — Shogo Sasaki
(74) *Attorney, Agent, or Firm* — Snell & Wilmer L.L.P.

(57) ABSTRACT

The system utilizes a laboratory data management system (LDMS), a medical data management system (MDMS) and external data sources. The system processes data across multiple laboratories, different input variables (lab assays), specific laboratory tests, specific laboratory testing capabilities and variable outputs. The system measures, documents and manages the immune response by providing the user with actionable laboratory results, triggers and events.

19 Claims, 8 Drawing Sheets

IMMUNITY TRACKING SYSTEM

CROSS-REFERENCE TO RELATED APPLICATIONS

This application is a continuation of, claims priority to and the benefit of, U.S. Ser. No. 17/329,771 filed May 25, 2021 and entitled "IMMUNE PATHWAY MANAGEMENT SYSTEM," which is now U.S. Pat. No. 11,281,194 issued Mar. 22, 2022, and which is hereby incorporated by reference in its entirety for all purposes.

FIELD

This disclosure generally relates to an immune pathway management system, and more particularly, to measuring, documenting and managing the immune response by providing actionable laboratory results and events.

BACKGROUND

A laboratory system typically only receives specific specimens from a treating physician, analyzes the specimens, and delivers the test results to all stakeholders as a singular defined event. The results are typically delivered to the stakeholders using a Laboratory Information Management System (LIMS). As such, each laboratory and its associated LIMS traditionally work as a siloed entity in this entire process.

Subsequent laboratory tests are only initiated from the physician side. In other words, the physician may request additional laboratory tests, but only after the physician determines that the results are abnormal based on standardized controls. The laboratory and its associated pathologist(s) often determine such standardized controls.

Pathologists for each laboratory typically define the parameters of normal variances versus abnormal variances for each assay. These parameters can change based on a variety of different variables including, for example, changing variances, changing outputs defined in studies, literature and laboratory governance (FDA, CLIA). As such, the data output from the LIMS is often highly variable and often not standardized. Furthermore, different LIMS systems exist on the market, and each of the LIMS systems may interface with the different types of lab assays and the different machines that analyze and process the lab assays. Moreover, different types of lab assays are being commercially developed (known as laboratory developed tests). Analysis devices may receive widely variable input (lab assays), conduct widely divergent processing, include widely divergent analyzing components, produce variable outputs and create varied data formatting in order to provide a final test result.

Such laboratory tests may be associated with a person's immune pathway. The human body's response to external and genetically determined internal triggers (stimuli) results in an immune response. The immune response may result in a multitude of physiologic responses which can involve multiple organs (or organ systems). The triggering event within this cascade of responses may be identified by a variety of complex molecular pathology tests. Depending on the pathologic entity (problem) that is being tested, the test may be a EUA test (emergency use authorization test—approved by the FDA) or a LDT (laboratory developed test—created by a specific laboratory following mandatory lab validation guidelines for certified labs). These molecular pathology tests can be widely variable in the type of specimen collected from the patient, the type of assay, the type of processing machine, the type of analyzer, and the type of data output at each step along the way. Many of these tests may undergo refinements and updates. The results of these tests may trigger additional laboratory examinations for evaluation or correlation to other physiologic processes (e.g., heart rate, heart rhythm disturbances, blood glucose measurements, oxygen saturation, etc.). For example, quantification of neutralizing activities (e.g., neutralizing antibodies) are currently the only means to test for immunity to COVID-19. Associated binding antibodies (non-neutralizing) generated as part of the immune response do not prevent virus penetration and subsequent infection of the host cell. The neutralizing antibodies are the only antibody that prevents the virus from entering the cells. An example is the C-Pass test which measures the percentage of neutralizing antibodies specific to SARS-CoV-2 infections. A positive C-Pass test indicates that greater than 30% neutralizing activity exists, which provides 120 days of protection before needing to be re-tested. These parameters are defined by the current literature and will potentially change as further research is published.

A strong need exists for a system that may address such variable and changing laboratory processes in an automated fashion with adaptability to a rapidly changing environment, along with trigger events delivered via a mobile application interface to the user (e.g., patient).

SUMMARY

In various embodiments, the method may include receiving, by a processor in communication with a laboratory data management system, a specimen; analyzing, by the processor in communication with the laboratory data management system, the specimen; determining, by the processor in communication with the laboratory data management system, a result based on the analyzing; providing, by the processor in communication with the laboratory data management system, the result to a medical data management system; providing, by the processor in communication with external data sources, data to the medical data management system; and providing, by the processor in communication with the medical data management system, event triggers.

The method may further include providing the results in a health card. The method may further include determining a frequency of testing the specimen. The method may further include determining additional vaccinations are needed to avoid the result being negative. The specimen may include at least one of molecular pathology specimens, genetic test specimens, routine lab test specimens or pathology specimens.

The event triggers may be determined by at least one of artificial intelligence, machine learning or algorithms. The event triggers may be based on lab assays. The event triggers may include actionable results of subsequent testing recommendations. The event triggers may include at least one of notifications, alerts, signals, messaging or direct communications with healthcare providers.

The result may include at least one of user information, a lab test processing sequence, a pathologist analysis, the laboratory test or the laboratory results. The providing the result to the medical data management system may include providing the result in real-time. The method may further include converting the result into a standardized data and processing format. The method may further include providing the result to a translator. The method may further include providing the result to a laboratory information management system. The method may further include adapting the translator to at least one of different laboratories, different laboratory information management systems or different results. The analyzing the specimen may be based on at least one of specimen type, lab test type, associated conditions, associated lab tests, associated external monitors or management of current tests. The data may comprise at least one of medical images, videos, test results or medical monitoring information.

BRIEF DESCRIPTION OF DRAWINGS

A more complete understanding of the present disclosure may be derived by referring to the detailed description and claims when considered in connection with the Figures, wherein like reference numbers refer to similar elements throughout the Figures, and:

DETAILED DESCRIPTION

Figure 1:
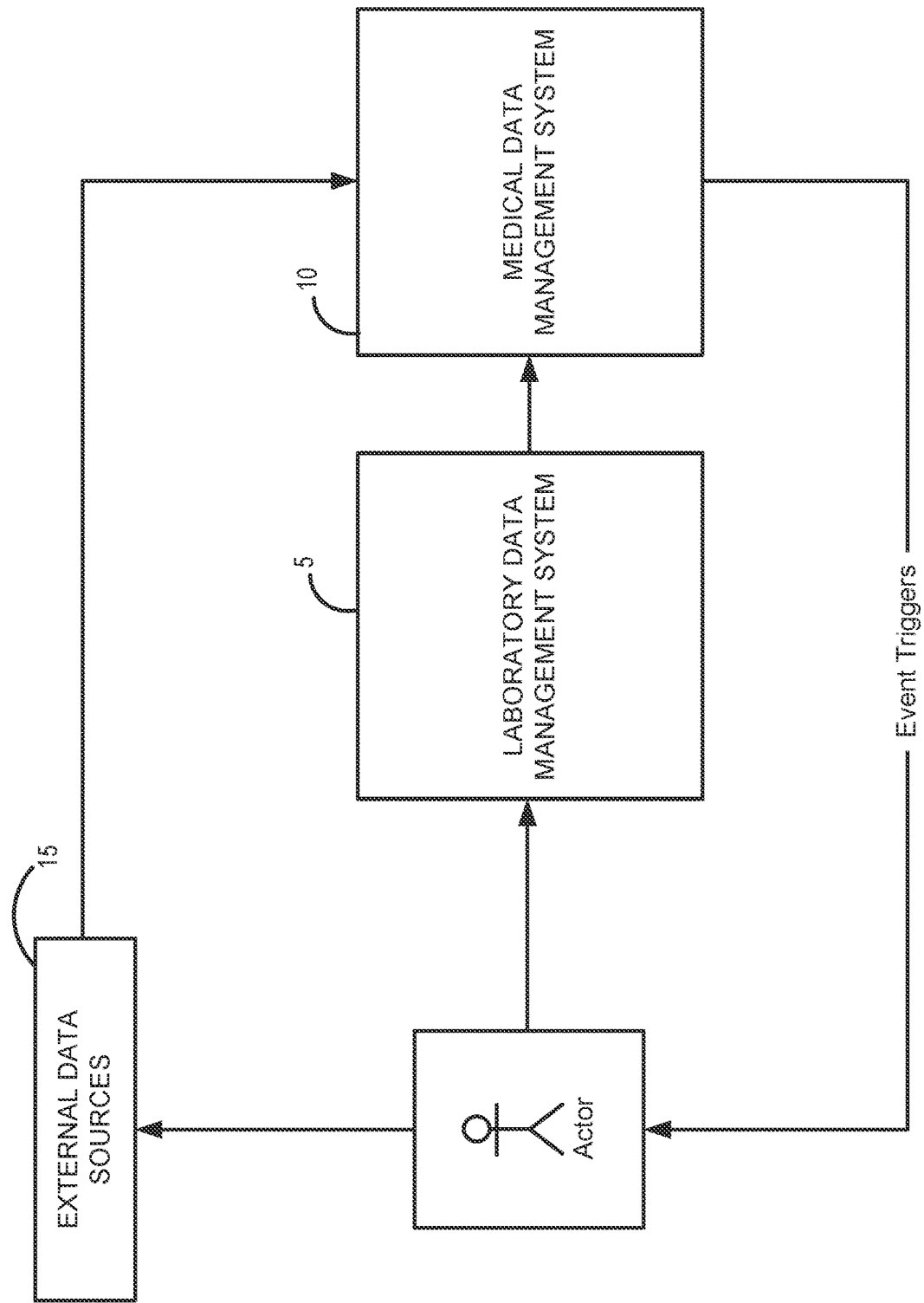
FIG. 1 is an exemplary high-level overview of an immune pathway management system that includes a laboratory data management system and a medical data management system, in accordance with various embodiments.

In general, and with reference to FIG. 1, the system may utilize a laboratory data management system (LDMS 5), a medical data management system (MDMS 10) and external data sources 15. In various embodiments, the system may process data across multiple laboratories, different input variables (lab assays), specific laboratory tests, specific laboratory testing capabilities and variable outputs. The user may provide (or the user's healthcare provider may provide on behalf of the user) specimens to the LDMS 5. The user may also provide information to (or the information may be acquired by) the external data sources 15. The LDMS 5 may provide results and other information to the MDMS 10. The external data sources 15 may also provide data to the MDMS 10. The MDMS 10 may provide event triggers to the user. As such, in response to the laboratory equipment and technicians completing certain tests (using blood, tissue, etc.), the system may interface with the laboratory equipment such that the system may, based on the input from the laboratory equipment, provide the testing results, initiate triggers, request re-tests, deactivate a health card, etc. One or more of the components of the system may include software, hardware, a platform, app, micro-app, algorithms, modules, etc. The app may operate on any platform such as, for example, the IOS or Android platforms. The system may process multiple tests simultaneously.

The triggers may be determined by the use of artificial intelligence, machine learning and other algorithms. The pathologic literature may help to define accepted parameters of testing, outputs and relevance to the associated disease process. This can be correlated with the existing and associated disease states that have known treatment and evaluation algorithms. The data collected and analyzed by the system provide an ideal interface for machine learning. Long term follow-up of a large patient population on the app may provide data which can be processed to define treatment and analysis algorithms which can correlate with the published literature. The process and analysis may adjust over time, since the field of immunology is a rapidly evolving field.

The system may be agnostic to and/or interface with any laboratory, test, assay and/or Laboratory Information Management System (LIMS). In other words, the system may process any type of assay as these tests evolve. Laboratory assays for disease states are constantly evolving. The assays themselves and the machines to process and analyze them can vary. The parameters for normal and abnormal are typically defined only after adherence to regulatory analysis and standardization protocols. The purpose of the LIMS system is to output the processed result in a defined manner. The LIMS system is typically able to interface with the processing and analysis hardware and software and adapt to changing assays. Moreover, the system may be lab assay specific in that the system may deliver assay analysis results on a health card 40 and adjust the analysis based on multi-factorial feedback analyzed by the MDMS 10. For example, the pathologist may determine the frequency of testing or additional vaccinations are needed because of associated conditions (e.g., Immunocompromised patients, chemotherapy patients). As noted above, published literature may define a decision tree algorithm. An example of this involves the neutralizing antibody test for SARS-CoV-2. Published literature may indicate that immunocompromised patients may require a higher percentage of neutralizing antibody than the normal population to be immune, and their duration of immunity may be shorter. Based on this information, the IMMUNOPASS card may adjust the expiration date to a shorter interval, and adjust the "positive" reading to a higher percentage of neutralizing antibody. Based on data collected over time, including long term testing, the system may include a machine learning component to adapt to not only the literature but the evolving results of the patients being tested in the system.

The system may also provide real-time laboratory processing updates and real-time notifications. The system may receive (e.g., in real time) such laboratory processing updates and/or notifications from a LIMS. The system may scan any indicator (e.g., a bar code or QR code). The indicator may be located on a health card and/or on a test kit. The scanning may create and/or submit a requisition to a laboratory for testing a specimen. The system may also scan a claim bar code. After scanning the bar code, the system may display the lab information, the clinic information, the bar code data, the particular requisition, the type of specimen and the type of test. The system may also provide order entry questions for the user to complete to obtain more data from the user. The questions may determine if the user is an exposure risk for the virus. The app may also disclose the storage type (e.g., ice pack) and if the user is requesting a first immunity test. After the information is verified, the system may register the test kit. The data collection may be configurable and/or specific to a particular clinic, hospital system, clinical trial or employer. The system may provide (e.g., via an app interface) a workflow or status update (e.g., in real time). For example, for a particular test order, the system may provide a status indicator showing that the order was created, the specimen was collected, the lab received the specimen, the lab reviewed and/or processed the specimen and the test was completed.

As set forth in more detail below, the system may also include user triggers based on specific lab assays. The triggers may include actionable results such as, for example, subsequent testing follow-up based on accepted guidelines of efficacy defined by the regulatory agencies. Such triggers may be in the form of notifications, alerts, signals, messaging or direct communications with a healthcare provider (HCP).

Figure 2:
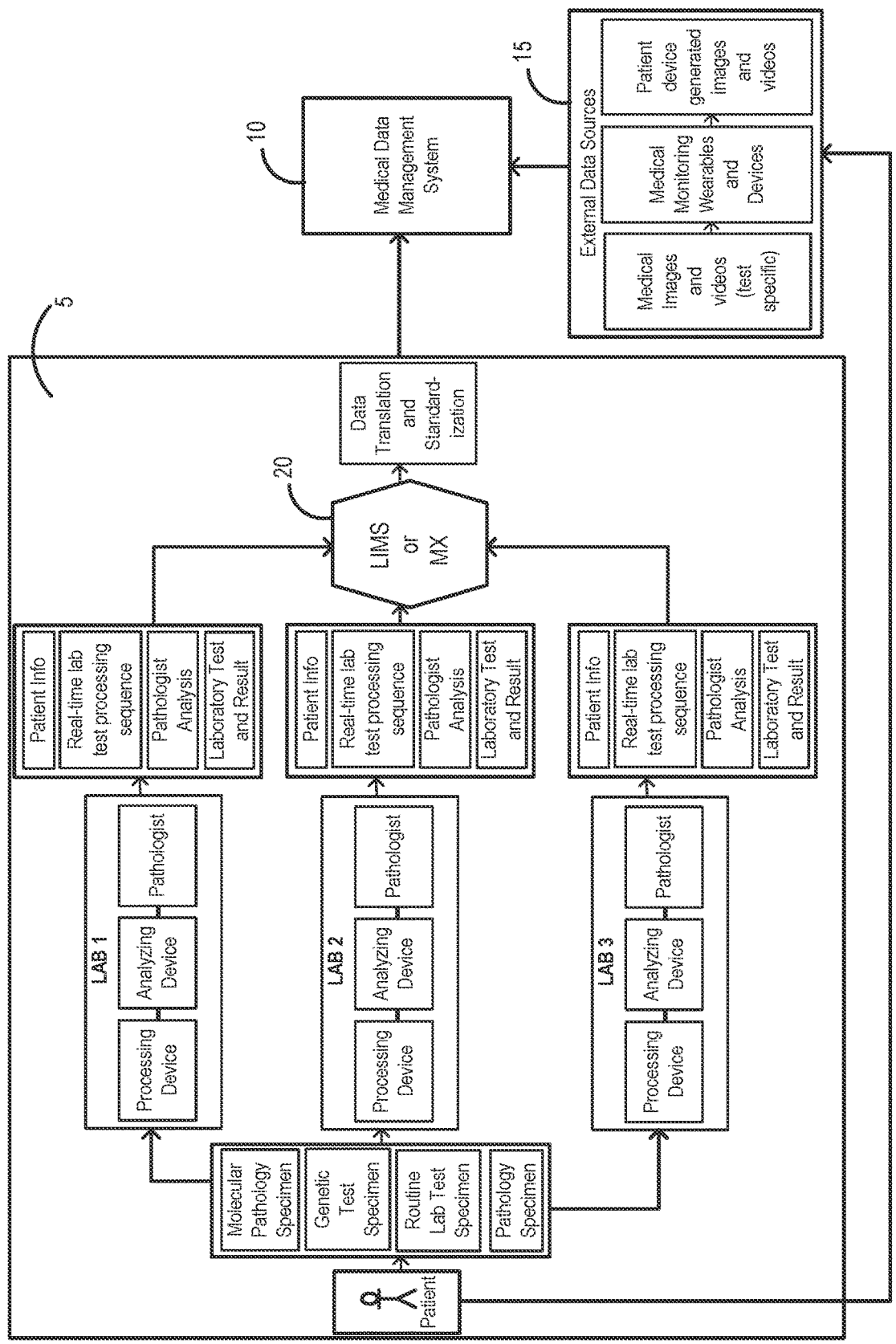
FIG. 2 is an exemplary detailed overview of the laboratory data management system of FIG. 1, in accordance with various embodiments.

With reference to FIG. 2, the user may provide (or the user's healthcare provider may provide for the user) specimens to one or more laboratories. Such specimens may include, for example, molecular pathology specimens, genetic test specimens, routine lab test specimens and/or pathology specimens. The laboratories may process and analyze the specimens using one or more processing devices, one or more analyzing devices and one or more pathologists. The pathologists may analyze the lab results, translate the lab results and/or determine triggers for the user. In various embodiments, the laboratory may provide laboratory information such as, for example, the user information, a lab test processing sequence (e.g., real-time), a pathologist analysis, the laboratory test and/or the laboratory results. The LDMS 5 may present such information to the MDMS 10 so that the MDMS 10 may determine a series of triggers associated with a laboratory test and the final result from the laboratory test. Certain lab tests are indicative of testing for the presence or absence of certain disease states and their severity. Abnormal results are indicative certain pathologic processes and can generate additional tests for further evaluation. An example is a positive COVID test which will potentially generate a series of additional tests as this disease state can involve multiple other organ systems.

With respect to FIG. 2, within the LDMS 5, the laboratory information may be provided to a translator 20 and/or a LIMS. In various embodiments, the system may be configured to use an LIMS which not only processes the outputs of different assays (delivering results to stakeholders in a standardized fashion that defines parameters of normal versus abnormal), but also translates events, outputs and parameters to the MDMS (mobile app). With respect to the configuration of the Health Cards, these outputs are customized for each assay based on consultation with the pathologist. These output parameters may be defined by the system to be configurable and could potentially be adjusted based on ongoing analysis of current literature, input by the pathologist and analysis of data in the system. Legacy LIMS systems typically need an intermediate step to get the data processed, so this system may use a "translator" (e.g., MX translator). The outputs from these systems is not standardized and needs to be converted to a "readable format" before being available. Once converted, the data will be processed in a similar fashion to data from the LIMS.

The LDMS 5 may include a translator 20 or translation interface (e.g., an EVE MX translator 20). Such a translation interface may convert the diverse processes and diverse data from the various labs (and the assays that they perform) into a standardized data and processing format. As such, the translator 20 may provide data translation and standardization. The translator 20 may adapt to different laboratories, different laboratory companies, different LIMSs and/or different processed outputs. As such, the LDMS 5 may translate, standardize and/or organize the myriad of different test results for processing and analysis by the MDMS 10. In particular, the LDMS 5 handles each type of lab test individually dependent on multiple parameters. Such parameters may include, for example, specimen type (e.g., serum, saliva, tissue), lab test type (molecular pathology, genetic, standard chemistries, microscopic etc.), associated conditions (defines additional tests and monitoring devices), associated lab tests (defined by associated conditions), associated external monitors (defined by associated conditions) and/or management of current tests. The management of current tests may include, for example, recommended user actions based on the analysis of the variety of immunological test results, associated laboratories and external data inputs from the user.

In various embodiments, and with reference to FIGS. 1 and 2, external data may be sent to the MDMS 10. The MDMS 10 may acquire or receive such external data from the external data sources 15. The external data sources 15 may include, for example, medical images, videos, test results, etc. Such items may be test-specific results. The external data sources 15 may also include medical monitoring devices such as, for example, medical monitoring wearables and other medical monitoring devices. The external data sources 15 may also include user device generated images and videos. For example, the user may use a smartphone or other recorder to take images or videos of certain health conditions.

Figure 3:
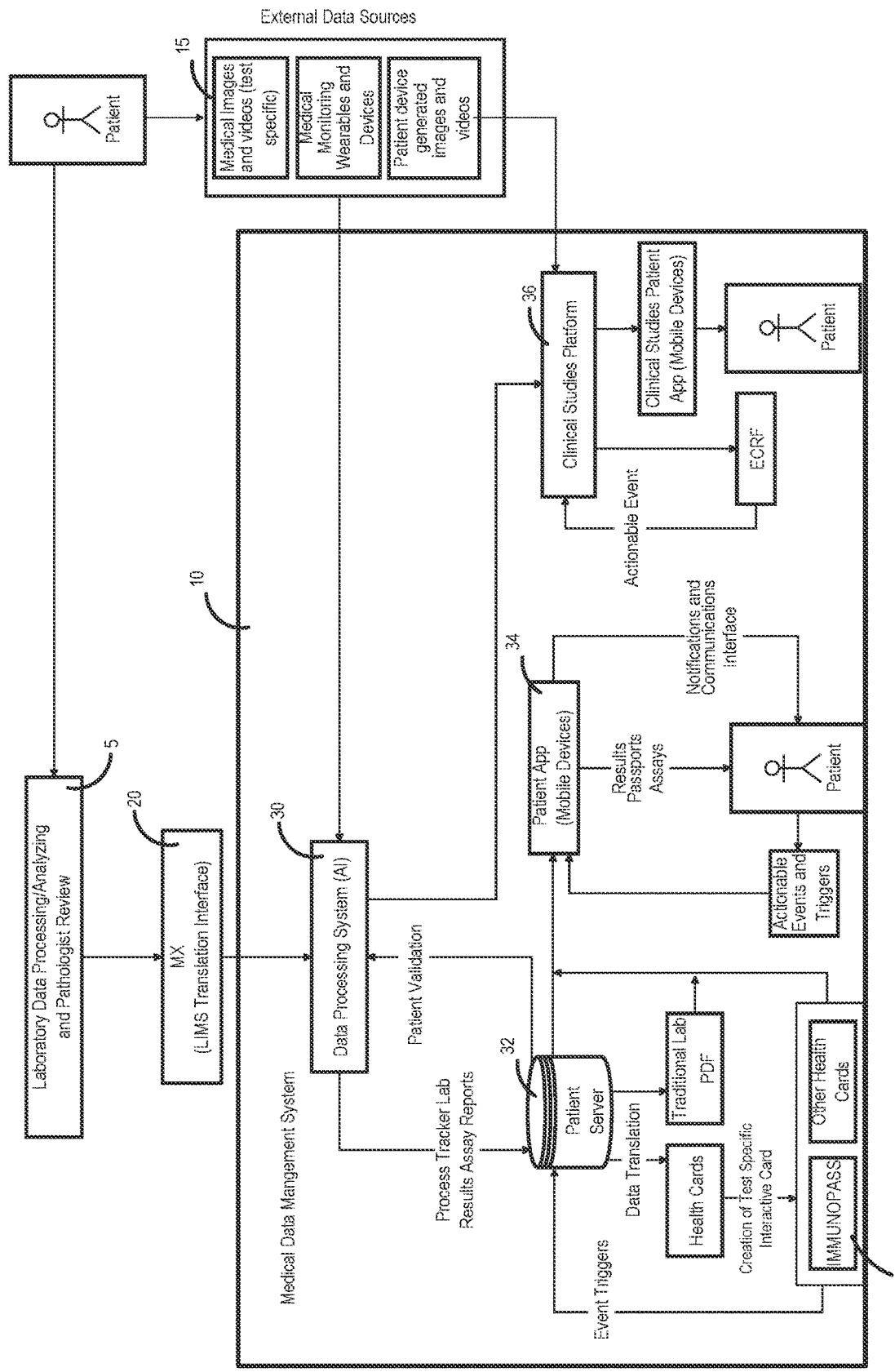
FIG. 3 is an exemplary detailed overview of the medical data management system of FIG. 1, in accordance with various embodiments.

In various embodiments, and with reference to FIG. 3, the MDMS 10 may be any data processing system or method. The MDMS 10 may be integrated into the system along with the LDMS 5 and the external data sources 15. The MDMS 10 may receive, acquire, correlate and/or process all inputs from the LDMS 5 and/or external data sources 15. The MDMS 10 may correlate the feeds from the LDMS 5 and/or the external data sources 15 with known associations with other disease processes related to a processed result. COVID has a myriad of different symptoms ranging from fevers and malaise to multi-organ inflammatory responses. There appears to be a genetic predisposition to these more systemic symptoms yet to be defined. For example, based on this premise, a patient may have a genetic profile test on the app, wherein the profile defines an increased chance of systemic symptoms. A positive COVID test could then create a cascade on data extraction from monitoring devices (e.g., heart rate, Oxygen saturation, blood sugar, etc.), additional testing recommended, a message (or update) to the physician, recommendations (and updates) for additional testing and suggestions to the patients on next steps.

The immunopathology space often has new and evolving assays whose final outputs are variable depending on accepted parameters defined by regulatory agencies governing these types of tests. As such, the MDMS 10 may send triggers, in response to changing variables with the processing and analysis system of a laboratory and also in response to the changing variables associated with a test (as defined by the pathologist associated with that particular assay). The MDMS 10 may create actionable items associated with variable triggers. Certain changes in any of the above parameters may be predefined and may trigger events such as, for example, additional testing, extraction of data from external monitoring devices, and/or communications with the physician. Using a mobile technology platform, the system may function as an information sharing and communication interface The MDMS 10 may include a data processing system 30 that utilizes artificial intelligence. The data processing system 30 may receive input from the LDMS 5 (via a translation interface) and from the external data sources 15. The data processing system 30 sends the process tracker, lab results and assay reports to a user server 32. The process tracker is the steps of the testing process, from receipt by the lab, to final result completed for the test. The patient can open the app and get the status of their test (similar to a pizza delivery tracker or a package delivery tracker). After completion, the results and assay reports are delivered from the LIMS to the app and are stored for the patient to reference at any time. The user server 32 may conduct user validation processes. The user server 32 may provide data translation of the data and send the data to the health cards 40. The health cards 40 may be in the form of an app, software and/or GUI. The user server 32 may also convert the data into a traditional lab report (e.g., in the form of a PDF report). The health card 40 may include an Immuno-Pass and/or other health cards. The health cards 40 may provide event triggers to the user server 32. The user server 32 and/or health cards 40 may send data to the user app 34 (e.g., on the user mobile device). The user app 34 may provide the results, passports and/or assays to the user. The user app 34 may also provide notifications to the user and/or serve as a communications interface. The user may send actionable events and/or triggers to the user app 34. External devices are examples of triggers from the patient to the system. Other examples are any types of configurable forms or surveys that can trigger the event, such as symptoms of shortness of breath. The system may include configurable surveys. The surveys may be pre-test surveys and/or patient surveys, and the data may be entered by the patient into the app.

A clinical studies platform 36 may also receive data from the external sources and the data processing system 30. The clinical studies platform 36 may send data to the clinical studies user app 34, which provides information to the user via the user's mobile device. The clinical studies platform 36 may also provide data to the eCRF (electronic clinical research forms). eCRF are structured data collection forms in a clinical study and the eCRF provides actionable events to the clinical studies platform 36. Clinical trials are typically a highly structured process that analyzes the safety and efficacy of a device or a pharma product. Laboratory tests results are a critical part of the process (e.g., elevated liver function tests after drug treatment). The system provides a direct connection to the laboratories and can automate triggers to the principal investigator and the clinical studies team (provided by the sponsor). These types of events (known as safety signals) may trigger a sequence of forms and further evaluations by the physician.

In various embodiments, the MDMS 10 may provide event triggers. The event triggers may receive input from multiple sources such as, for example, real-time laboratory processing data. The event triggers may be fully or partially integrated with a mobile app technology interface to the user. The event triggers may trigger the providing of information. For example, the event triggers may cause health cards 40 to be provided within an app. MDMS 10 may consider multi-factorial states when generating the health cards 40. Such states may include, for example, associated disease, related tests required, and additional information generated by external monitors. The health cards 40 may function as the event triggering feature to the user. The health cards 40 may have a test-specific interactive interface which processes the data sources, defines the test result, provides communication interfaces to appropriate medical specialists and/or provides access to additional testing modalities. With respect to specialists, certain disease states benefit from an evaluation by specialists. A telemedicine interface with the platform of the system provides a straightforward way of virtual communication with the appropriate specialist. This provides immediate actionable events for the patient. The ability to do this with a laboratory interface with real time lab updates and immediate triggers is ideal in the current medical environment.

The health card 40 may appear on the user interface in the app and analyze data specific to a specific immunologic test. Such data may include, for example, test results, up-to-date results analysis which can be adjusted in real time based on multiple variables, associated relevant data from monitoring devices, recommended relevant media inputs (e.g., audio, images, and video), relevant recommendations and information from the pathologist regarding the test, communications access to an HCP and/or recommendations of additional tests or testing frequency.

The system may be particularly helpful for the COVID-19 pathway. The COVID-19 virus has a spike protein on the virus surface that penetrates the cell and results in a myriad of inflammatory symptoms with multi-organ involvement. Multiple tests exist, are being updated and/or are being developed (including tests associated with molecular pathology, pathology, genetics and the laboratory) that detect such inflammatory symptoms. The pathophysiology of disease transmission and sequelae are not completely understood resulting in a rapidly changing immunopathology testing and analysis environment. This is especially true with the issue of intermediate and long-term immunity of the vaccinated and the COVID-19 exposed user. As such, the MDMS 10 may consider the various changes and provide triggers to the user to perform additional tests, as discussed above.

For example, with respect to the neutralizing activity (e.g., neutralizing antibody) test, several variables exist that may require a variable results output delivered by the system. The variables may change the output based on current literature and acceptance of the medical community of the accepted standard of care for that particular test. Such variables may include, for example, percentage of neutralizing activity, what percentage is effective in maintaining immunity, how long will this immunity persist, etc.

In various embodiments, an initial lab assay (test type) may trigger the MDMS 10 to assemble a database of associated medical conditions, external data sources 15, associated testing and algorithms for management. The MDMS 10 may determine what to assemble based on, for example, the initial test type in a look-up table. Such a look-up table may be defined by an expert on that assay. The look-up table may also be automatically configured based on ML/AI. The trigger may also activate a physician communication interface. The final test result may cause the triggers based on variable workflows which are dependent on current best practices and published medical literature. The pathologist may change variables associated with the test result and the system may automatically adjust to these changes and adjust all the above workflows. These changes may occur at the level of the laboratory analysis by the pathologist and is configured in the data output to the LIMS. The end result may be reflected in the Health card 40.

For example, with respect to the SARS COV-2 antigen test, the system may provide different triggers. Trigger 1 may determine if it is best for the user to obtain a Saliva test vs a Nasal swab test. This trigger may calculate the margin of error of negative versus a positive test based on specimen type and published statistics. Most lab tests and assays have published margins of error that can be used to calculate the best option. The result may be reflected in the Health card 40 that is generated. The results and the data may adjust according to the statistical data analysis of the different types of lab assays from each lab. Trigger 2 may include a positive test that triggers the MDMS 10 system to query all external devices, associated diagnoses, suggested additional testing, pathologist recommendations and commentary. To obtain some of the data, the MDMS 10 may also establish a communication connection with an HCP (Health Care Provider) through the mobile device. The system may establish the connection via being connected to a telemedicine platform. Telemedicine platforms have specialists that can be available virtually 24 hours a day. Triggers of abnormal lab events can also result in patient requests for more information. Additional datapoints may be requested from the user to define further workflows. All of this data and functionality may be included in the Health card 40. Trigger 3 may establish a direct real-time communication to the lab processing workflow via the mobile app.

In various embodiments, the processed output of the health card 40 and its associated features may be defined by the health card's 40 integration with the LDMS 5 and MDMS 10. Such integration may create a real-time generation of critical data and actionable events that provide timely responses to disease processes and that are directly related to a changing disease process. Such data and actionable events are delivered directly to the user. The health card 40 may be considered active based on a quantifiable event. A quantifiable event may be defined as the person having a certain amount of neutralizing activity as in the ImmunoPass feature of the health card 40. For example, as mentioned above, the person having greater than 30% neutralizing activity. Because it is known that the neutralizing activity may drop below 30% after 120 days, the health card 40 may automatically become inactive after 120 days. Moreover, the system may notify the user to obtain a new test before 120 days to avoid having the health card 40 become inactive. After the health card 40 becomes inactive, the user will need to get re-tested to determine if the person has greater than 30% neutralizing activity in order to obtain a new health card 40. As set forth in FIGS. 5A-D, in various embodiments, the system may provide an app that includes an interface showing different configurable health cards. The app interface may also show the percentage of neutralizing activity, provide an attachment for the pathologist's evaluation, provide access to all lab test results, provide a configurable expiration date for the ImmunoPass. The app interface may also show a configurable indicator of the amount of time left before another test is needed (e.g., the indicator may also include warning levels such as red, yellow, green. a reduction of time to expiration of the timeframe for testing for neutralizing activities. The app may provide a notification to re-test a certain time period before expiration (e.g., 1 week before). The app may provide a link to initiate a re-test. In that regard, the link may automatically activate a module or process that schedules an appointment. After the expiration period, the app may deactivate the healthcard until a positive neutralizing activity re-test is obtained. The deactivation of the health card may result in visually showing the health card is deactivated and is grayed out.

In various embodiments, the health cards 40 may include any card, interface and/or functionality associated with any medical or health issue, and may provide any of the data or functionality discussed herein. For example, the health card 40 may include ImmunoPass, Covid 19 Card, Vaccine Card, Genetic Testing Card, an Immunization Card, and Immunopathology tests, along with other health data or health-related functionality. The health card 40 may be configurable. The health card 40 may be configured to comply with all HIPAA requirements and functionality. The health card 40 and/or the system may also include or facilitate a payment functionality, transactional functionality and/or insurance reimbursement functionality.

Figure 4:
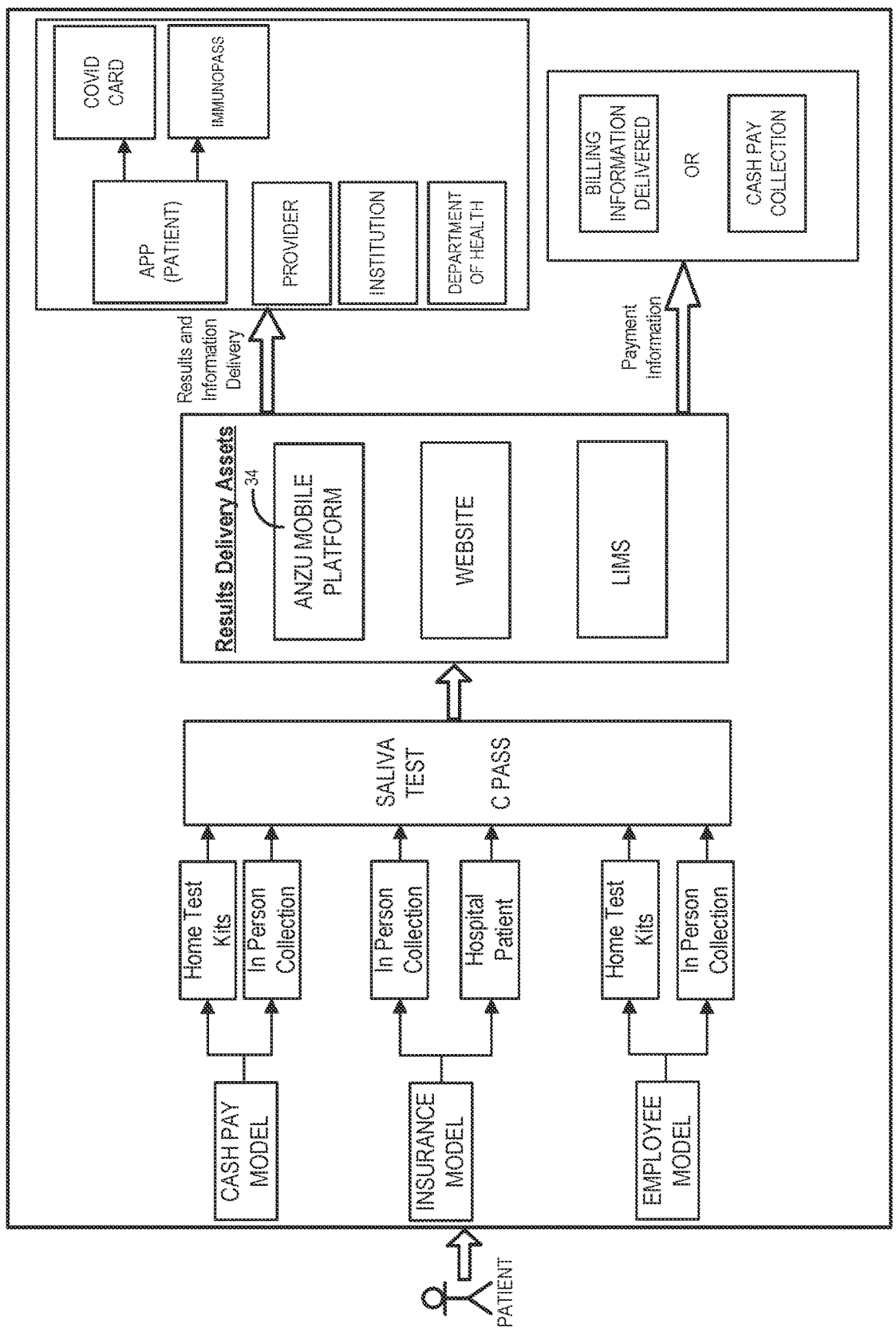
FIG. 4 is an exemplary data flow diagram of the transactional workflow, in accordance with various embodiments.
Figure 5A:
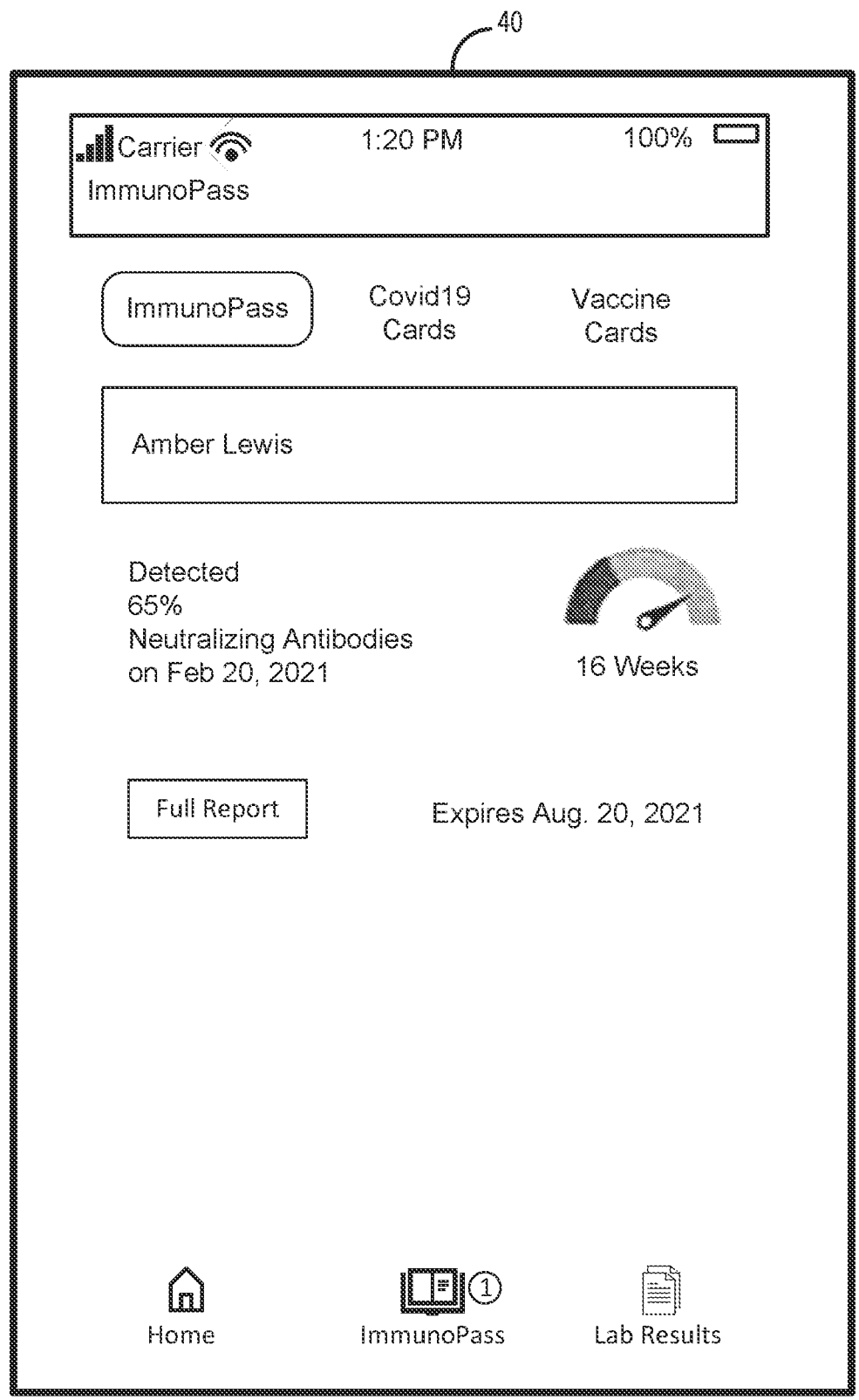
FIG. 5A-D are exemplary screen shots of apps showing a reduction of time to expiration of the timeframe for testing for neutralizing activities, in accordance with various embodiments.
Figure 5B:
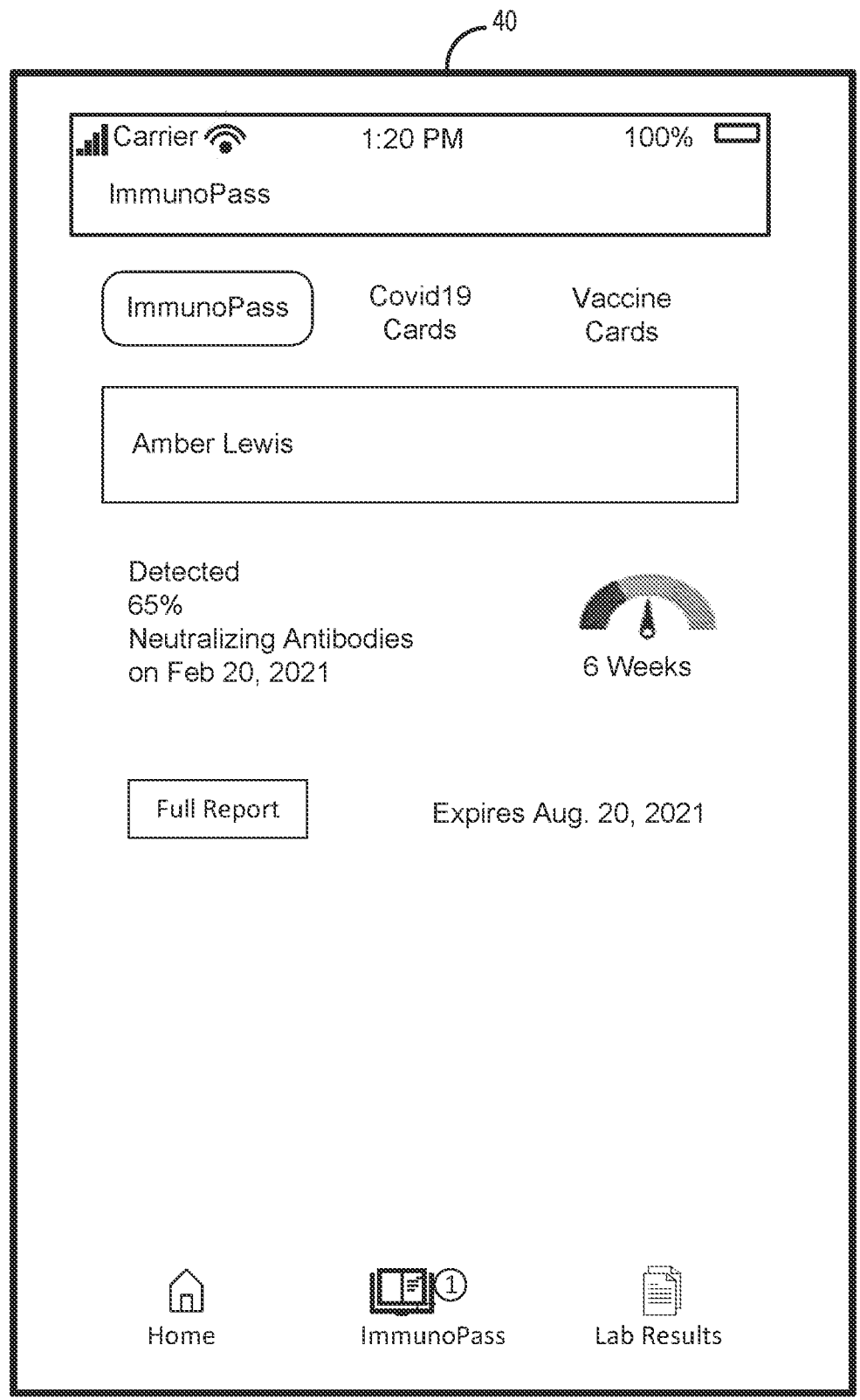
Figure 5C:
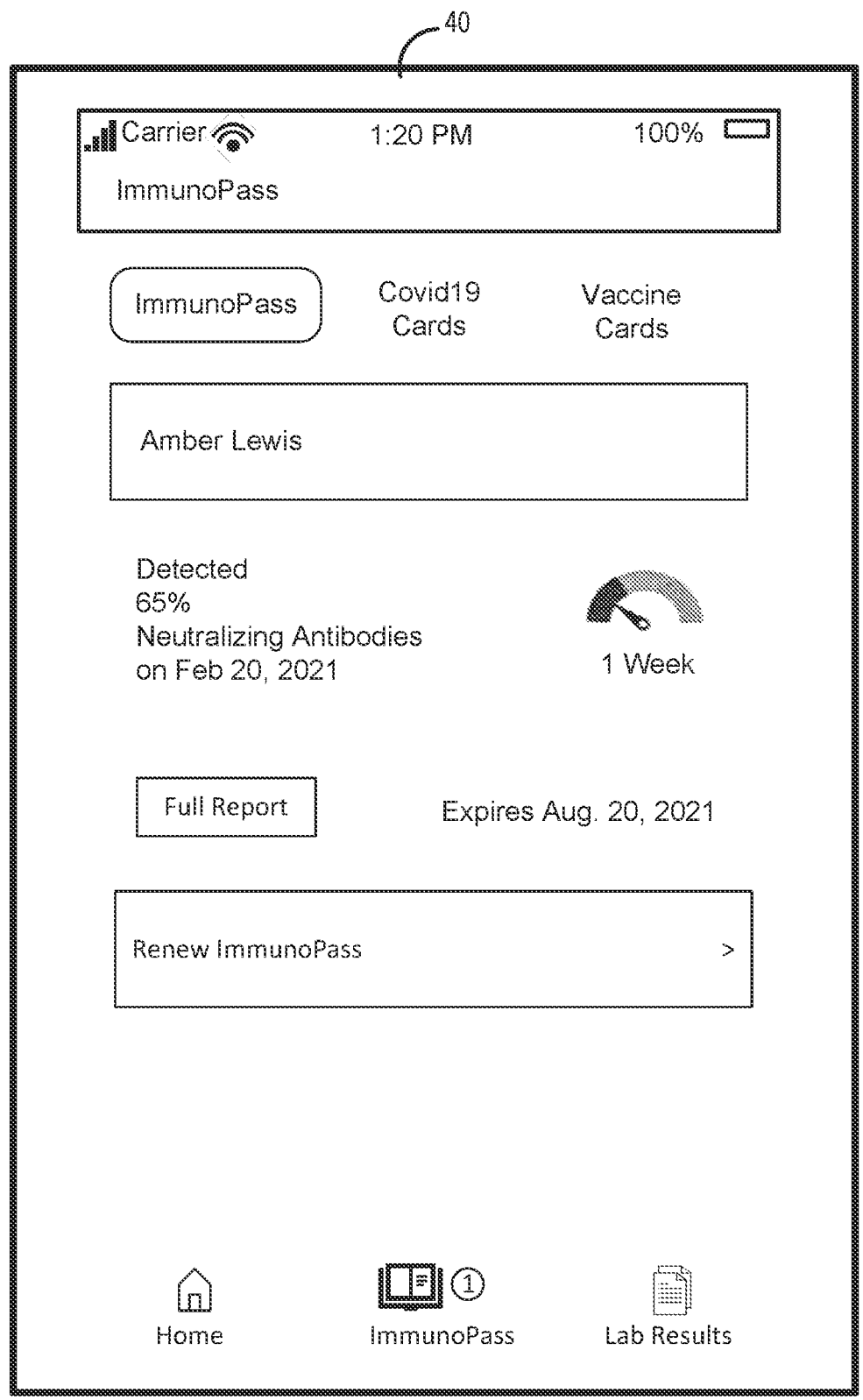
Figure 5D:
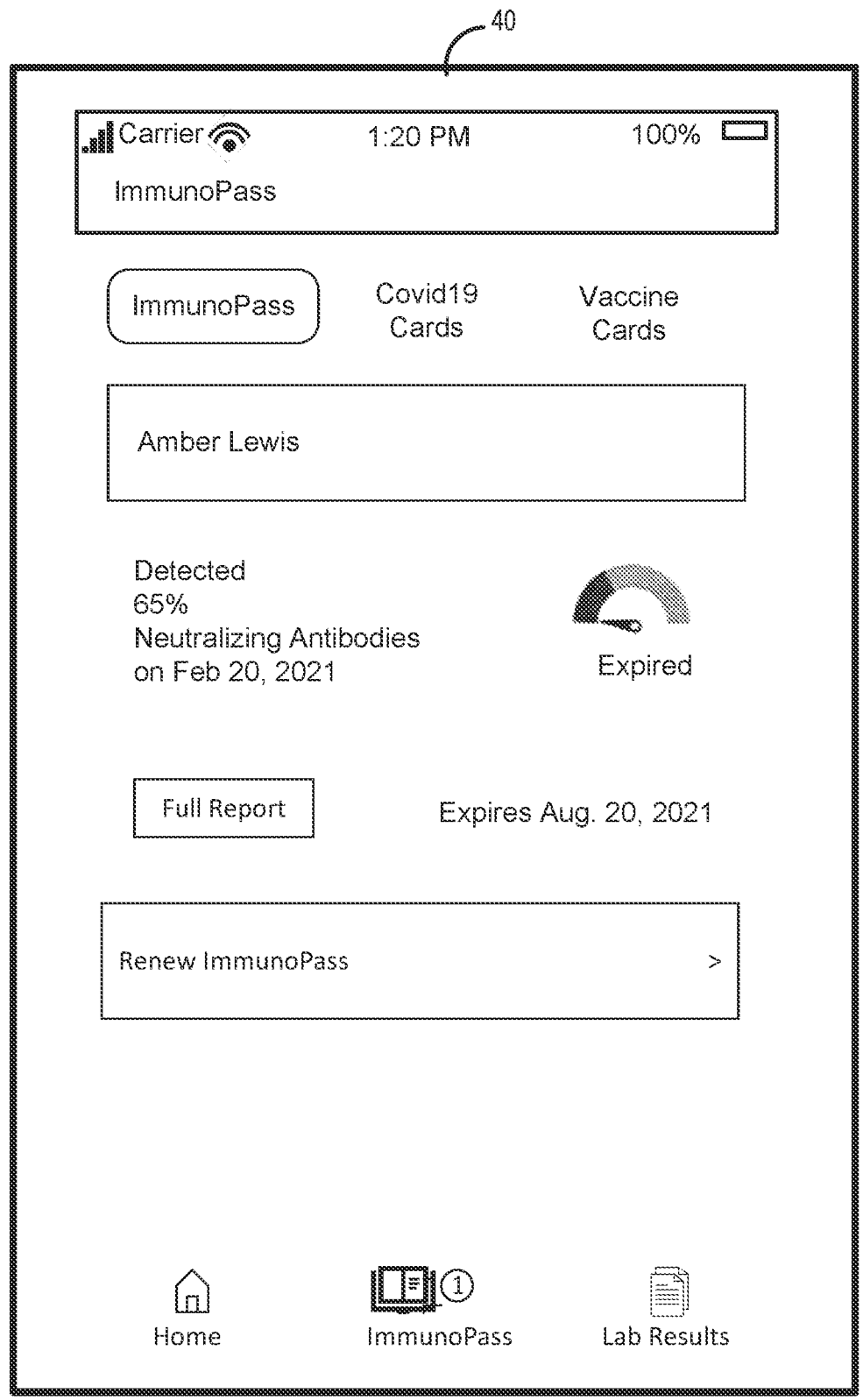

In various embodiments, with reference to FIG. 4, the system may also include a transactional component and/or a transactional interface. The transactional interface may be maintained by, for example, the accession.me website-based platform. The system and/or the mobile platform may also be configured for LIMS integration. The mobile platform may collect insurance information. The LIMS may integrate with the mobile platform and/or the accession.com website-based platform. The LIMS may also share insurance transactions with a billing platform. The system may include configurable billing profiles (e.g., via accession.me). This transactional platform adapts to the changing environment of the current immunopathology marketplace allowing a variety of different transactional models.

In various embodiments, the system may define a transactional cohort such as, for example, a cash pay model, an employee model or an insurance model. The system may also define a transactional type such as, for example, home test kit, hospital patient or personal collection. The home test kits may be a direct to consumer (cash pay) model which may provide greater flexibility in the system for collecting and analyzing tests. In various embodiments, the system may include a self-service capability at home for patients to get tests either by a machine or a home test kit. By analyzing the process, the system may provide recommendations and establish communication (telemedicine) for lab data results in real time. As testing kits become more available, the system may provide for rapid testing analysis and actionable events related to immune issues and their sequelae. The insurance transactional model may be a health care driven model that may identify cohorts of users that require additional testing modalities depending on risk factor analysis and immune testing results. The system may analyze coverage. In particular, certain high-risk groups may merit certain types of tests, while healthy individuals may not merit similar tests. This may be a function of cost control. The employer model may follow a similar premise as the insurance cohort, and may be driven to maintain a safe workspace environment. By integrating with the LIMS interface and the mobile app, these cohorts can be identified and the payment/billing gateways for each cohort may be configurable and/or automated depending on clinic, hospital system, insurer and/or employer. The clinic, hospital system, and/or employer may identify the cohorts and the cohorts may be configured in the LIMS.

In various embodiments, any of the models or transactional types enable samples (e.g., saliva test, C Pass) to be provided to the results delivery assets (e.g., mobile platform, website, LIMS). The results delivery assets may include the technology asset that serves as the information delivery vehicle. The results and information may be delivered to the user app 34 and/or various stakeholders. The stakeholders may include, for example, the provider, an institution and/or the Department of Health. The user app 34 may generate or update the health card 40, COVID card or ImmunoPass. The payment information may be delivered to a system for billing the user or for collecting cash from the user.

Some of the benefits of the system may be highlighted in various case studies. For example, in a first case, a 62 year old female with triple negative breast cancer received her first Pfizer vaccine dose, on Jan. 19, 2021 and her second dose on Feb. 9, 2021. She started chemo three days later, but she should have waited at least two weeks for the vaccine mediated immune response. Her neutralizing activity test on Feb. 26, 2021 was negative for neutralizing activity. Therefore, the system may determine that the immunomodulating or immunotoxic therapy for a wide range of health disorders (e.g., Cancer, COPD, Rheumatoid Arthritis) should be monitored and documented for immune competence to vaccine, prior to and during treatment.

In a second case, a 31 year old Emergency Room Physician experienced a prior moderate to severe symptomatic infection on Nov. 28, 2020. 90 days after the infection, the doctor refuses to get vaccinated, despite the offer of incentive pay. His neutralizing activity test taken of Apr. 12, 2021 shows 87% activity. The results are submitted to occupational health, so he can continue to work. He can re-submit in 120 days and he does not need to constantly obtain a COVID19 test. Up to 50% of healthcare workers and 35% of the general population are reticent to get a vaccine. However, a previous COVID19 infection may provide significant protection and reduce the pressure to get vaccinated. Moreover, based on input from the system, contracting with the employee to get a vaccine only after the loss of neutralizing activities is mutually beneficial and may lead to more compliance.

In a third case, a 69 year old nursing home patient with a history of Multiple Sclerosis obtained the Pfizer vaccine in November. She receives a negative neutralizing activity test in January. She repeats the Pfizer vaccine series in January. She again receives a negative neutralizing activity test in February. She receives the new J&J vaccine in March. She then receives a positive test for neutralizing activity with 52% activity. The system may help the doctors conclude that patients that are immunologically abnormal have multiple copies of certain genes (NLRP1), are immunosuppressed due to medications or age, and/or may simply lack the cellular mechanisms to process RNA vaccines. As such, these individuals should be offered a non-RNA vaccine as an alternative.

In a fourth case, large 12,000+ crowds at a convention (along with hotel staff, convention staff, bars and restaurants) are also tested with high vaccine penetrance may interact with networking sessions, recruiting dinners, and vendor demonstrations. To reduce the risk, each of the individuals are screened for neutralizing activities. Those that are positive are cleared for minimum of 120 days. Those that are negative are required to obtain a COVID test (PCR) within 72 hours before attending the event and obtain a daily antigen test. As such, the neutralizing activity test allows a long enough lead time to clear large conventions and reduce worry amongst staff and participants.

In various embodiments, components, modules, and/or engines of system may be implemented as micro-applications or micro-apps. Micro-apps are typically deployed in the context of a mobile operating system, including for example, a WINDOWS® mobile operating system, an ANDROID® operating system, an APPLE® iOS operating system, a BLACKBERRY® company's operating system, and the like. The micro-app may be configured to leverage the resources of the larger operating system and associated hardware via a set of predetermined rules which govern the operations of various operating systems and hardware resources. For example, where a micro-app desires to communicate with a device or network other than the mobile device or mobile operating system, the micro-app may leverage the communication protocol of the operating system and associated device hardware under the predetermined rules of the mobile operating system. Moreover, where the micro-app desires an input from a user, the micro-app may be configured to request a response from the operating system which monitors various hardware components and then communicates a detected input from the hardware to the micro-app.

The system and method may be described herein in terms of functional block components, screen shots, optional selections, and various processing steps. It should be appreciated that such functional blocks may be realized by any number of hardware and/or software components configured to perform the specified functions. For example, the system may employ various integrated circuit components, e.g., memory elements, processing elements, logic elements, look-up tables, and the like, which may carry out a variety of functions under the control of one or more microprocessors or other control devices. Similarly, the software elements of the system may be implemented with any programming or scripting language such as C, C++, C #, JAVA®, JAVASCRIPT®, JAVASCRIPT® Object Notation (JSON), VBScript, Macromedia COLD FUSION, COBOL, MICROSOFT® company's Active Server Pages, assembly, PERL®, PHP, awk, PYTHON®, Visual Basic, SQL Stored Procedures, PL/SQL, any UNIX® shell script, and extensible markup language (XML) with the various algorithms being implemented with any combination of data structures, objects, processes, routines or other programming elements. Further, it should be noted that the system may employ any number of conventional techniques for data transmission, signaling, data processing, network control, and the like. Still further, the system could be used to detect or prevent security issues with a client-side scripting language, such as JAVASCRIPT®, VBScript, or the like.

The system and method are described herein with reference to screen shots, block diagrams and flowchart illustrations of methods, apparatus, and computer program products according to various embodiments. It will be understood that each functional block of the block diagrams and the flowchart illustrations, and combinations of functional blocks in the block diagrams and flowchart illustrations, respectively, can be implemented by computer program instructions.

Accordingly, functional blocks of the block diagrams and flowchart illustrations support combinations of means for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, can be implemented by either special purpose hardware-based computer systems which perform the specified functions or steps, or suitable combinations of special purpose hardware and computer instructions. Further, illustrations of the process flows and the descriptions thereof may make reference to user WINDOWS® applications, webpages, websites, web forms, prompts, etc. Practitioners will appreciate that the illustrated steps described herein may comprise, in any number of configurations, including the use of WINDOWS® applications, webpages, web forms, popup WINDOWS® applications, prompts, and the like. It should be further appreciated that the multiple steps as illustrated and described may be combined into single webpages and/or WINDOWS® applications but have been expanded for the sake of simplicity. In other cases, steps illustrated and described as single process steps may be separated into multiple webpages and/or WINDOWS® applications but have been combined for simplicity.

In various embodiments, the software elements of the system may also be implemented using a JAVASCRIPT® run-time environment configured to execute JAVASCRIPT® code outside of a web browser. For example, the software elements of the system may also be implemented using NODE. JS® components. NODE.JS® programs may implement several modules to handle various core functionalities. For example, a package management module, such as NPM®, may be implemented as an open source library to aid in organizing the installation and management of third-party NODE.JS® programs. NODE.JS® programs may also implement a process manager, such as, for example, Parallel Multithreaded Machine ("PM2"); a resource and performance monitoring tool, such as, for example, Node Application Metrics ("appmetrics"); a library module for building user interfaces, and/or any other suitable and/or desired module.

Middleware may include any hardware and/or software suitably configured to facilitate communications and/or process transactions between disparate computing systems. Middleware components are commercially available and known in the art. Middleware may be implemented through commercially available hardware and/or software, through custom hardware and/or software components, or through a combination thereof. Middleware may reside in a variety of configurations and may exist as a standalone system or may be a software component residing on the internet server. Middleware may be configured to process transactions between the various components of an application server and any number of internal or external systems for any of the purposes disclosed herein. WEBSPHERE® MQ™ (formerly MQSeries) by IBM®, Inc. (Armonk, N.Y.) is an example of a commercially available middleware product. An Enterprise Service Bus ("ESB") application is another example of middleware.

The computers discussed herein may provide a suitable website or other internet-based graphical user interface which is accessible by users. In one embodiment, MICROSOFT® company's Internet Information Services (IIS), Transaction Server (MTS) service, and an SQL SERVER® database, are used in conjunction with MICROSOFT® operating systems, WINDOWS NT® web server software, SQL SERVER® database, and MICROSOFT® Commerce Server. Additionally, components such as ACCESS® software, SQL SERVER® database, ORACLE® software, SYBASE® software, INFORMIX® software, MYSQL® software, INTERBASE® software, etc., may be used to provide an Active Data Object (ADO) compliant database management system. In one embodiment, the APACHE® web server is used in conjunction with a LINUX® operating system, a MYSQL® database, and PERL®, PHP, Ruby, and/or PYTHON® programming languages.

For the sake of brevity, conventional data networking, application development, and other functional aspects of the systems (and components of the individual operating components of the systems) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in a practical system.

In various embodiments, the system and various components may integrate with one or more smart digital assistant technologies. For example, exemplary smart digital assistant technologies may include the ALEXA® system developed by the AMAZON® company, the GOOGLE HOME® system developed by Alphabet, Inc., the HOMEPOD® system of the APPLE® company, and/or similar digital assistant technologies. The ALEXA® system, GOOGLE HOME® system, and HOMEPOD® system, may each provide cloud-based voice activation services that can assist with tasks, entertainment, general information, and more. All the ALEXA® devices, such as the AMAZON ECHO®, AMAZON ECHO DOT®, AMAZON TAP®, and AMAZON FIRE® TV, have access to the ALEXA® system. The ALEXA® system, GOOGLE HOME® system, and HOMEPOD® system may receive voice commands via its voice activation technology, activate other functions, control smart devices, and/or gather information. For example, the smart digital assistant technologies may be used to interact with music, emails, texts, phone calls, question answering, home improvement information, smart home communication/activation, games, shopping, making to-do lists, setting alarms, streaming podcasts, playing audiobooks, and providing weather, traffic, and other real time information, such as news. The ALEXA®, GOOGLE HOME®, and HOMEPOD® systems may also allow the user to access information about eligible transaction accounts linked to an online account across all digital assistant-enabled devices.

The various system components discussed herein may include one or more of the following: a host server or other computing systems including a processor for processing digital data; a memory coupled to the processor for storing digital data; an input digitizer coupled to the processor for inputting digital data; an application program stored in the memory and accessible by the processor for directing processing of digital data by the processor; a display device coupled to the processor and memory for displaying information derived from digital data processed by the processor; and a plurality of databases. Various databases used herein may include: client data; merchant data; financial institution data; and/or like data useful in the operation of the system. As those skilled in the art will appreciate, user computer may include an operating system (e.g., WINDOWS®, UNIX®, LINUX®, SOLARIS®, MACOS® etc.) as well as various conventional support software and drivers typically associated with computers.

The present system or any part(s) or function(s) thereof may be implemented using hardware, software, or a combination thereof and may be implemented in one or more computer systems or other processing systems. However, the manipulations performed by embodiments may be referred to in terms, such as matching or selecting, which are commonly associated with mental operations performed by a human operator. No such capability of a human operator is necessary, or desirable, in most cases, in any of the operations described herein. Rather, the operations may be machine operations or any of the operations may be conducted or enhanced by artificial intelligence (AI) or machine learning. AI may refer generally to the study of agents (e.g., machines, computer-based systems, etc.) that perceive the world around them, form plans, and make decisions to achieve their goals. Foundations of AI include mathematics, logic, philosophy, probability, linguistics, neuroscience, and decision theory. Many fields fall under the umbrella of AI, such as computer vision, robotics, machine learning, and natural language processing. Useful machines for performing the various embodiments include general purpose digital computers or similar devices.

In various embodiments, the embodiments are directed toward one or more computer systems capable of carrying out the functionalities described herein. The computer system includes one or more processors. The processor is connected to a communication infrastructure (e.g., a communications bus, cross-over bar, network, etc.). Various software embodiments are described in terms of this exemplary computer system. After reading this description, it will become apparent to a person skilled in the relevant art(s) how to implement various embodiments using other computer systems and/or architectures. The computer system can include a display interface that forwards graphics, text, and other data from the communication infrastructure (or from a frame buffer not shown) for display on a display unit.

The computer system also includes a main memory, such as random access memory (RAM), and may also include a secondary memory. The secondary memory may include, for example, a hard disk drive, a solid-state drive, and/or a removable storage drive. The removable storage drive reads from and/or writes to a removable storage unit in a well-known manner. As will be appreciated, the removable storage unit includes a computer usable storage medium having stored therein computer software and/or data.

In various embodiments, secondary memory may include other similar devices for allowing computer programs or other instructions to be loaded into a computer system. Such devices may include, for example, a removable storage unit and an interface. Examples of such may include a program cartridge and cartridge interface (such as that found in video game devices), a removable memory chip (such as an erasable programmable read only memory (EPROM), programmable read only memory (PROM)) and associated socket, or other removable storage units and interfaces, which allow software and data to be transferred from the removable storage unit to a computer system.

The computer system may also include a communications interface. A communications interface allows software and data to be transferred between the computer system and external devices. Examples of such a communications interface may include a modem, a network interface (such as an Ethernet card), a communications port, etc. Software and data transferred via the communications interface are in the form of signals which may be electronic, electromagnetic, optical, or other signals capable of being received by communications interface. These signals are provided to communications interface via a communications path (e.g., channel). This channel carries signals and may be implemented using wire, cable, fiber optics, a telephone line, a cellular link, a radio frequency (RF) link, wireless and other communications channels.

In various embodiments, the server may include application servers (e.g., WEBSPHERE®, WEBLOGIC®, JBOSS®, POSTGRES PLUS ADVANCED SERVER®, etc.). In various embodiments, the server may include web servers (e.g., Apache, IIS, GOOGLE® Web Server, SUN JAVA® System Web Server, JAVA® Virtual Machine running on LINUX® or WINDOWS® operating systems).

A web client includes any device or software which communicates via any network, such as, for example any device or software discussed herein. The web client may include internet browsing software installed within a computing unit or system to conduct online transactions and/or communications. These computing units or systems may take the form of a computer or set of computers, although other types of computing units or systems may be used, including personal computers, laptops, notebooks, tablets, smart phones, cellular phones, personal digital assistants, servers, pooled servers, mainframe computers, distributed computing clusters, kiosks, terminals, point of sale (POS) devices or terminals, televisions, or any other device capable of receiving data over a network. The web client may include an operating system (e.g., WINDOWS®, WINDOWS MOBILE® operating systems, UNIX® operating system, LINUX® operating systems, APPLE® OS® operating systems, etc.) as well as various conventional support software and drivers typically associated with computers. The web-client may also run MICROSOFT® INTERNET EXPLORER® software, MOZILLA® FIREFOX® software, GOOGLE CHROME' software, APPLE® SAFARI® software, or any other of the myriad software packages available for browsing the internet.

As those skilled in the art will appreciate, the web client may or may not be in direct contact with the server (e.g., application server, web server, etc., as discussed herein). For example, the web client may access the services of the server through another server and/or hardware component, which may have a direct or indirect connection to an internet server. For example, the web client may communicate with the server via a load balancer. In various embodiments, web client access is through a network or the internet through a commercially-available web-browser software package. In that regard, the web client may be in a home or business environment with access to the network or the internet. The web client may implement security protocols such as Secure Sockets Layer (SSL) and Transport Layer Security (TLS). A web client may implement several application layer protocols including HTTP, HTTPS, FTP, and SFTP.

The various system components may be independently, separately, or collectively suitably coupled to the network via data links which includes, for example, a connection to an Internet Service Provider (ISP) over the local loop as is typically used in connection with standard modem communication, cable modem, DISH NETWORK®, ISDN, Digital Subscriber Line (DSL), or various wireless communication methods. It is noted that the network may be implemented as other types of networks, such as an interactive television (ITV) network. Moreover, the system contemplates the use, sale, or distribution of any goods, services, or information over any network having similar functionality described herein.

The system contemplates uses in association with web services, utility computing, pervasive and individualized computing, security and identity solutions, autonomic computing, cloud computing, commodity computing, mobility and wireless solutions, open source, biometrics, grid computing, and/or mesh computing.

Any of the communications, inputs, storage, databases or displays discussed herein may be facilitated through a website having web pages. The term "web page" as it is used herein is not meant to limit the type of documents and applications that might be used to interact with the user. For example, a typical website might include, in addition to standard HTML documents, various forms, JAVA® applets, JAVASCRIPT® programs, active server pages (ASP), common gateway interface scripts (CGI), extensible markup language (XML), dynamic HTML, cascading style sheets (CSS), AJAX (Asynchronous JAVASCRIPT And XML) programs, helper applications, plug-ins, and the like. A server may include a web service that receives a request from a web server, the request including a URL and an IP address (192.168.1.1). The web server retrieves the appropriate web pages and sends the data or applications for the web pages to the IP address. Web services are applications that are capable of interacting with other applications over a communications means, such as the internet. Web services are typically based on standards or protocols such as XML, SOAP, AJAX, WSDL and UDDI. Web services methods are well known in the art, and are covered in many standard texts. For example, representational state transfer (REST), or RESTful, web services may provide one way of enabling interoperability between applications.

The computing unit of the web client may be further equipped with an internet browser connected to the internet or an intranet using standard dial-up, cable, DSL, or any other internet protocol known in the art. Transactions originating at a web client may pass through a firewall in order to prevent unauthorized access from users of other networks. Further, additional firewalls may be deployed between the varying components of CMS to further enhance security.

Encryption may be performed by way of any of the techniques now available in the art or which may become available—e.g., Twofish, RSA, El Gamal, Schorr signature, DSA, PGP, PKI, GPG (GnuPG), HPE Format-Preserving Encryption (FPE), Voltage, Triple DES, Blowfish, AES, MD5, HMAC, IDEA, RC6, and symmetric and asymmetric cryptosystems. The systems and methods may also incorporate SHA series cryptographic methods, elliptic curve cryptography (e.g., ECC, ECDH, ECDSA, etc.), and/or other post-quantum cryptography algorithms under development.

The firewall may include any hardware and/or software suitably configured to protect CMS components and/or enterprise computing resources from users of other networks. Further, a firewall may be configured to limit or restrict access to various systems and components behind the firewall for web clients connecting through a web server. Firewall may reside in varying configurations including Stateful Inspection, Proxy based, access control lists, and Packet Filtering among others. Firewall may be integrated within a web server or any other CMS components or may further reside as a separate entity. A firewall may implement network address translation ("NAT") and/or network address port translation ("NAPT"). A firewall may accommodate various tunneling protocols to facilitate secure communications, such as those used in virtual private networking. A firewall may implement a demilitarized zone ("DMZ") to facilitate communications with a public network such as the internet. A firewall may be integrated as software within an internet server or any other application server components, reside within another computing device, or take the form of a standalone hardware component.

Any databases discussed herein may include relational, hierarchical, graphical, blockchain, object-oriented structure, and/or any other database configurations. Any database may also include a flat file structure wherein data may be stored in a single file in the form of rows and columns, with no structure for indexing and no structural relationships between records. For example, a flat file structure may include a delimited text file, a CSV (comma-separated values) file, and/or any other suitable flat file structure. Common database products that may be used to implement the databases include DB2® by IBM® (Armonk, N.Y.), various database products available from ORACLE® Corporation (Redwood Shores, Calif.), MICROSOFT ACCESS® or MICROSOFT SQL SERVER® by MICROSOFT® Corporation (Redmond, Wash.), MYSQL® by MySQL AB (Uppsala, Sweden), MONGODB Redis, APACHE CASSANDRA®, HBASE® by APACHE®, MapR-DB by the MAPR® corporation, or any other suitable database product. Moreover, any database may be organized in any suitable manner, for example, as data tables or lookup tables. Each record may be a single file, a series of files, a linked series of data fields, or any other data structure.

As used herein, big data may refer to partially or fully structured, semi-structured, or unstructured data sets including millions of rows and hundreds of thousands of columns. A big data set may be compiled, for example, from a history of purchase transactions over time, from web registrations, from social media, from records of charge (ROC), from summaries of charges (SOC), from internal data, or from other suitable sources. Big data sets may be compiled without descriptive metadata such as column types, counts, percentiles, or other interpretive-aid data points.

Association of certain data may be accomplished through any desired data association technique such as those known or practiced in the art. For example, the association may be accomplished either manually or automatically. Automatic association techniques may include, for example, a database search, a database merge, GREP, AGREP, SQL, using a key field in the tables to speed searches, sequential searches through all the tables and files, sorting records in the file according to a known order to simplify lookup, and/or the like. The association step may be accomplished by a database merge function, for example, using a "key field" in pre-selected databases or data sectors. Various database tuning steps are contemplated to optimize database performance. For example, frequently used files such as indexes may be placed on separate file systems to reduce In/Out ("I/O") bottlenecks.

More particularly, a "key field" partitions the database according to the high-level class of objects defined by the key field. For example, certain types of data may be designated as a key field in a plurality of related data tables and the data tables may then be linked on the basis of the type of data in the key field. The data corresponding to the key field in each of the linked data tables is preferably the same or of the same type. However, data tables having similar, though not identical, data in the key fields may also be linked by using AGREP, for example. In accordance with one embodiment, any suitable data storage technique may be utilized to store data without a standard format. Data sets may be stored using any suitable technique, including, for example, storing individual files using an ISO/IEC 7816-4 file structure; implementing a domain whereby a dedicated file is selected that exposes one or more elementary files containing one or more data sets; using data sets stored in individual files using a hierarchical filing system; data sets stored as records in a single file (including compression, SQL accessible, hashed via one or more keys, numeric, alphabetical by first tuple, etc.); data stored as Binary Large Object (BLOB); data stored as ungrouped data elements encoded using ISO/IEC 7816-6 data elements; data stored as ungrouped data elements encoded using ISO/IEC Abstract Syntax Notation (ASN.1) as in ISO/IEC 8824 and 8825; other proprietary techniques that may include fractal compression methods, image compression methods, etc.

In various embodiments, the ability to store a wide variety of information in different formats is facilitated by storing the information as a BLOB. Thus, any binary information can be stored in a storage space associated with a data set. As discussed above, the binary information may be stored in association with the system or external to but affiliated with the system. The BLOB method may store data sets as ungrouped data elements formatted as a block of binary via a fixed memory offset using either fixed storage allocation, circular queue techniques, or best practices with respect to memory management (e.g., paged memory, least recently used, etc.). By using BLOB methods, the ability to store various data sets that have different formats facilitates the storage of data, in the database or associated with the system, by multiple and unrelated owners of the data sets. For example, a first data set which may be stored may be provided by a first party, a second data set which may be stored may be provided by an unrelated second party, and yet a third data set which may be stored may be provided by a third party unrelated to the first and second party. Each of these three exemplary data sets may contain different information that is stored using different data storage formats and/or techniques. Further, each data set may contain subsets of data that also may be distinct from other subsets.

As stated above, in various embodiments, the data can be stored without regard to a common format. However, the data set (e.g., BLOB) may be annotated in a standard manner when provided for manipulating the data in the database or system. The annotation may comprise a short header, trailer, or other appropriate indicator related to each data set that is configured to convey information useful in managing the various data sets. For example, the annotation may be called a "condition header," "header," "trailer," or "status," herein, and may comprise an indication of the status of the data set or may include an identifier correlated to a specific issuer or owner of the data. In one example, the first three bytes of each data set BLOB may be configured or configurable to indicate the status of that particular data set; e.g., LOADED, INITIALIZED, READY, BLOCKED, REMOVABLE, or DELETED. Subsequent bytes of data may be used to indicate for example, the identity of the issuer, user, transaction/membership account identifier or the like. Each of these condition annotations are further discussed herein.

The data set annotation may also be used for other types of status information as well as various other purposes. For example, the data set annotation may include security information establishing access levels. The access levels may, for example, be configured to permit only certain individuals, levels of employees, companies, or other entities to access data sets, or to permit access to specific data sets based on the transaction, merchant, issuer, user, or the like. Furthermore, the security information may restrict/permit only certain actions, such as accessing, modifying, and/or deleting data sets. In one example, the data set annotation indicates that only the data set owner or the user are permitted to delete a data set, various identified users may be permitted to access the data set for reading, and others are altogether excluded from accessing the data set. However, other access restriction parameters may also be used allowing various entities to access a data set with various permission levels as appropriate.

The data, including the header or trailer, may be received by a standalone interaction device configured to add, delete, modify, or augment the data in accordance with the header or trailer. As such, in one embodiment, the header or trailer is not stored on the transaction device along with the associated issuer-owned data, but instead the appropriate action may be taken by providing to the user, at the standalone device, the appropriate option for the action to be taken. The system may contemplate a data storage arrangement wherein the header or trailer, or header or trailer history, of the data is stored on the system, device or transaction instrument in relation to the appropriate data.

One skilled in the art will also appreciate that, for security reasons, any databases, systems, devices, servers, or other components of the system may consist of any combination thereof at a single location or at multiple locations, wherein each database or system includes any of various suitable security features, such as firewalls, access codes, encryption, decryption, compression, decompression, and/or the like.

Practitioners will also appreciate that there are a number of methods for displaying data within a browser-based document. Data may be represented as standard text or within a fixed list, scrollable list, drop-down list, editable text field, fixed text field, pop-up window, and the like. Likewise, there are a number of methods available for modifying data in a web page such as, for example, free text entry using a keyboard, selection of menu items, check boxes, option boxes, and the like.

The data may be big data that is processed by a distributed computing cluster. The distributed computing cluster may be, for example, a HADOOP® software cluster configured to process and store big data sets with some of nodes comprising a distributed storage system and some of nodes comprising a distributed processing system. In that regard, distributed computing cluster may be configured to support a HADOOP® software distributed file system (HDFS) as specified by the Apache Software Foundation at www.hadoop.apache.org/docs.

As used herein, the term "network" includes any cloud, cloud computing system, or electronic communications system or method which incorporates hardware and/or software components. Communication among the parties may be accomplished through any suitable communication channels, such as, for example, a telephone network, an extranet, an intranet, internet, point of interaction device (point of sale device, personal digital assistant (e.g., an IPHONE® device, a BLACKBERRY® device), cellular phone, kiosk, etc.), online communications, satellite communications, off-line communications, wireless communications, transponder communications, local area network (LAN), wide area network (WAN), virtual private network (VPN), networked or linked devices, keyboard, mouse, and/or any suitable communication or data input modality. Moreover, although the system is frequently described herein as being implemented with TCP/IP communications protocols, the system may also be implemented using IPX, APPLETALK® program, IP-6, NetBIOS, OSI, any tunneling protocol (e.g. IPsec, SSH, etc.), or any number of existing or future protocols. If the network is in the nature of a public network, such as the internet, it may be advantageous to presume the network to be insecure and open to eavesdroppers. Specific information related to the protocols, standards, and application software utilized in connection with the internet is generally known to those skilled in the art and, as such, need not be detailed herein.

"Cloud" or "Cloud computing" includes a model for enabling convenient, on-demand network access to a shared pool of configurable computing resources (e.g., networks, servers, storage, applications, and services) that can be rapidly provisioned and released with minimal management effort or service provider interaction. Cloud computing may include location-independent computing, whereby shared servers provide resources, software, and data to computers and other devices on demand.

Any database discussed herein may comprise a distributed ledger maintained by a plurality of computing devices (e.g., nodes) over a peer-to-peer network. Each computing device maintains a copy and/or partial copy of the distributed ledger and communicates with one or more other computing devices in the network to validate and write data to the distributed ledger. The distributed ledger may use features and functionality of blockchain technology, including, for example, consensus-based validation, immutability, and cryptographically chained blocks of data. The blockchain may comprise a ledger of interconnected blocks containing data. The blockchain may provide enhanced security because each block may hold individual transactions and the results of any blockchain executables. Each block may link to the previous block and may include a timestamp. Blocks may be linked because each block may include the hash of the prior block in the blockchain. The linked blocks form a chain, with only one successor block allowed to link to one other predecessor block for a single chain. Forks may be possible where divergent chains are established from a previously uniform blockchain, though typically only one of the divergent chains will be maintained as the consensus chain. In various embodiments, the blockchain may implement smart contracts that enforce data workflows in a decentralized manner. The system may also include applications deployed on user devices such as, for example, computers, tablets, smartphones, Internet of Things devices ("IoT" devices), etc. The applications may communicate with the blockchain (e.g., directly or via a blockchain node) to transmit and retrieve data. In various embodiments, a governing organization or consortium may control access to data stored on the blockchain. Registration with the managing organization(s) may enable participation in the blockchain network.

Data transfers performed through the blockchain-based system may propagate to the connected peers within the blockchain network within a duration that may be determined by the block creation time of the specific blockchain technology implemented. For example, on an ETHEREUM®-based network, a new data entry may become available within about 13-20 seconds as of the writing. On a HYPERLEDGER® Fabric 1.0 based platform, the duration is driven by the specific consensus algorithm that is chosen, and may be performed within seconds. In that respect, propagation times in the system may be improved compared to existing systems, and implementation costs and time to market may also be drastically reduced. The system also offers increased security at least partially due to the immutable nature of data that is stored in the blockchain, reducing the probability of tampering with various data inputs and outputs. Moreover, the system may also offer increased security of data by performing cryptographic processes on the data prior to storing the data on the blockchain. Therefore, by transmitting, storing, and accessing data using the system described herein, the security of the data is improved, which decreases the risk of the computer or network from being compromised.

In various embodiments, the system may also reduce database synchronization errors by providing a common data structure, thus at least partially improving the integrity of stored data. The system also offers increased reliability and fault tolerance over traditional databases (e.g., relational databases, distributed databases, etc.) as each node operates with a full copy of the stored data, thus at least partially reducing downtime due to localized network outages and hardware failures. The system may also increase the reliability of data transfers in a network environment having reliable and unreliable peers, as each node broadcasts messages to all connected peers, and, as each block comprises a link to a previous block, a node may quickly detect a missing block and propagate a request for the missing block to the other nodes in the blockchain network.

The particular blockchain implementation described herein provides improvements over conventional technology by using a decentralized database and improved processing environments. In particular, the blockchain implementation improves computer performance by, for example, leveraging decentralized resources (e.g., lower latency). The distributed computational resources improves computer performance by, for example, reducing processing times. Furthermore, the distributed computational resources improves computer performance by improving security using, for example, cryptographic protocols.

Any communication, transmission, and/or channel discussed herein may include any system or method for delivering content (e.g. data, information, metadata, etc.), and/or the content itself. The content may be presented in any form or medium, and in various embodiments, the content may be delivered electronically and/or capable of being presented electronically. For example, a channel may comprise a website, mobile application, or device (e.g., FACEBOOK®, YOUTUBE®, PANDORA®, APPLE TV®, MICROSOFT® XBOX®, ROKU®, AMAZON FIRE®, GOOGLE CHROMECAST™, SONY® PLAYSTATION®, NINTENDO® SWITCH®, etc.) a uniform resource locator ("URL"), a document (e.g., a MICROSOFT® Word or EXCEL™, an ADOBE® Portable Document Format (PDF) document, etc.), an "ebook," an "emagazine," an application or microapplication (as described herein), an short message service (SMS) or other type of text message, an email, a FACEBOOK® message, a TWITTER® tweet, multimedia messaging services (MMS), and/or other type of communication technology. In various embodiments, a channel may be hosted or provided by a data partner. In various embodiments, the distribution channel may comprise at least one of a merchant website, a social media website, affiliate or partner websites, an external vendor, a mobile device communication, social media network, and/or location based service. Distribution channels may include at least one of a merchant website, a social media site, affiliate or partner websites, an external vendor, and a mobile device communication. Examples of social media sites include FACEBOOK®, FOURSQUARE®, TWITTER®, LINKEDIN®, INSTAGRAM®, PINTEREST®, TUMBLR®, REDDIT®, SNAPCHAT®, WHATSAPP®, FLICKR®, VK®, OZONE®, WECHAT®, and the like. Examples of affiliate or partner websites include AMERICAN EXPRESS®, GROUPON®, LIVINGSOCIAL®, and the like. Moreover, examples of mobile device communications include texting, email, and mobile applications for smartphones.

The detailed description of various embodiments herein makes reference to the accompanying drawings and pictures, which show various embodiments by way of illustration. While these various embodiments are described in sufficient detail to enable those skilled in the art to practice the disclosure, it should be understood that other embodiments may be realized and that logical and mechanical changes may be made without departing from the spirit and scope of the disclosure. Thus, the detailed description herein is presented for purposes of illustration only and not for purposes of limitation. For example, the steps recited in any of the method or process descriptions may be executed in any order and are not limited to the order presented. Moreover, any of the functions or steps may be outsourced to or performed by one or more third parties. Modifications, additions, or omissions may be made to the systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set. Furthermore, any reference to singular includes plural embodiments, and any reference to more than one component may include a singular embodiment.

Although specific advantages have been enumerated herein, various embodiments may include some, none, or all of the enumerated advantages.

Systems, methods, and computer program products are provided. In the detailed description herein, references to "various embodiments," "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the disclosure. The scope of the disclosure is accordingly limited by nothing other than the appended claims, in which reference to an element in the singular is not intended to mean "one and only one" unless explicitly so stated, but rather "one or more." Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Although the disclosure includes a method, it is contemplated that it may be embodied as computer program instructions on a tangible computer-readable carrier, such as a magnetic or optical memory or a magnetic or optical disk. All structural, chemical, and functional equivalents to the elements of the above-described various embodiments that are known to those of ordinary skill in the art are expressly incorporated herein by reference and are intended to be encompassed by the present claims. Moreover, it is not necessary for a device or method to address each and every problem sought to be solved by the present disclosure for it to be encompassed by the present claims. Furthermore, no element, component, or method step in the present disclosure is intended to be dedicated to the public regardless of whether the element, component, or method step is explicitly recited in the claims. No claim element is intended to invoke 35 U.S.C. § 112(f) unless the element is expressly recited using the phrase "means for" or "step for". As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

I claim:

1. A method comprising:
   receiving, by a processor, a result of an analysis of a specimen associated with data about health conditions of a subject, wherein the result of the analysis of the specimen is determined by a laboratory data management system; and adjusting, by the processor, and based on the data about the health conditions and the result, at least one of an expiration date for obtaining another neutralizing antibodies test, a percentage of neutralizing antibodies in the subject or a timeframe for the percentage of the neutralizing antibodies to be at a level to provide immunity to a disorder.

2. The method of claim 1, wherein the processor is in communication with at least one of a medical data management system or a laboratory data management system.

3. The method of claim 1, wherein the adjusting is further based upon data from external data sources about the health conditions of the subject.

4. The method of claim 1, wherein the adjusting is further based upon data from external data sources about the health conditions of the subject, and wherein the data comprises at least one of medical images, videos, test results or medical monitoring information.

5. The method of claim 1, wherein the adjusting is performed in at least one of a health app or in a health card.

6. The method of claim 1, further comprising determining, by the processor, at least one of a frequency of testing the subject, subsequent testing recommendations for the subject or additional vaccinations needed for the subject, based on the health conditions and the result.

7. The method of claim 1, further comprising determining, by the processor, an additional one or more vaccinations are needed for the subject to receive a negative result.

8. The method of claim 1, wherein an indicator is scanned on at least one of a health app, health card or test kit to obtain information about at least one of the specimen or the subject.

9. The method of claim 1, wherein an indicator is scanned on at least one of a health app, health card or test kit to at least one of create or submit a requisition to a laboratory for testing the specimen.

10. The method of claim 1, further comprising providing, by the processor, at least one of notifications, alerts, signals, messaging, status updates or direct communications with healthcare providers about the adjusting.

11. The method of claim 1, further comprising providing, by the processor, questions and obtaining answers to the questions to determine the health conditions of the subject.

12. The method of claim 1, further comprising obtaining, by the processor, at least one of monitoring data or genetic data about the subject, in response to a test disclosing that the subject is positive for the disorder.

13. The method of claim 1, further comprising converting, by the processor, the result into at least one of a standardized format of data or a standardized format for processing.

14. The method of claim 1, further comprising interfacing, by the processor in real-time, with at least one of a healthcare provider system, a laboratory system or a lab processing workflow.

15. The method of claim 1, wherein the adjusting is in response to the percentage of the neutralizing antibodies in the subject being above a threshold percentage.

16. The method of claim 1, further comprising adapting, by the processor in communication with a translator, the translator to at least one of different laboratories, different laboratory information management systems or different results.

17. The method of claim 1, further comprising providing, by the processor, a notification to re-test for the neutralizing antibodies, prior to the expiration date for obtaining the another neutralizing antibodies test.

18. An article of manufacture including a non-transitory, tangible computer readable storage medium having instructions stored thereon that, in response to execution by a processor, cause the processor to perform operations comprising:
   receiving, by the processor, a result of an analysis of a specimen associated with data about health conditions of a subject, wherein the result of the analysis of the specimen is determined by a laboratory data management system; and
   adjusting, by the processor, and based on the data about the health conditions and the result, at least one of an expiration date for obtaining another neutralizing antibodies test, a percentage of neutralizing antibodies in the subject or a timeframe for the percentage of the neutralizing antibodies to be at a level to provide immunity to a disorder.

19. A system comprising:
   a processor; and
   a tangible, non-transitory memory configured to communicate with the processor, the tangible, non-transitory memory having instructions stored thereon that, in response to execution by the processor, cause the processor to perform operations comprising:
   receiving, by the processor, a result of an analysis of a specimen associated with data about health conditions of a subject, wherein the result of the analysis of the specimen is determined by a laboratory data management system; and
   adjusting, by the processor, and based on the data about the health conditions and the result, at least one of an expiration date for obtaining another neutralizing antibodies test, a percentage of neutralizing antibodies in the subject or a timeframe for the percentage of the neutralizing antibodies to be at a level to provide immunity to a disorder.

\* \* \* \* \*